United States Patent
Constancis et al.

(10) Patent No.: US 6,790,438 B1
(45) Date of Patent: Sep. 14, 2004

(54) CROSS-LINKED COLLAGENIC PEPTIDE FOR PREVENTING POST-SURGICAL ADHESIONS

(75) Inventors: Alain Constancis, Lyons (FR); Remi Meyrueix, Lyons (FR)

(73) Assignee: Flamel Technologies (FR)

(*) Notice: Subject to any disclaimer, the term of this patent is extended or adjusted under 35 U.S.C. 154(b) by 0 days.

(21) Appl. No.: 09/914,424

(22) PCT Filed: Mar. 1, 2000

(86) PCT No.: PCT/FR00/00514
§ 371 (c)(1),
(2), (4) Date: Jan. 14, 2002

(87) PCT Pub. No.: WO00/51661
PCT Pub. Date: Sep. 8, 2000

(30) Foreign Application Priority Data

Mar. 2, 1999 (FR) .............................. 99 02728

(51) Int. Cl.⁷ .............................................. A61L 31/06
(52) U.S. Cl. .............................. 424/78.17; 128/DIG. 8; 514/21; 525/54.1; 530/356; 602/50; 604/289
(58) Field of Search .......................... 424/78.17; 514/8, 514/21; 530/356; 602/50; 106/160.1; 525/54.1; 128/DIG. 8; 604/289, 304, 307, 308, 309

(56) References Cited

U.S. PATENT DOCUMENTS

| | | | | | |
|---|---|---|---|---|---|
| 4,407,787 A | * | 10/1983 | Stemberger | .................. | 424/444 |
| 5,017,229 A | | 5/1991 | Burns et al. | .................. | 106/162 |
| 5,354,790 A | * | 10/1994 | Keusch et al. | .............. | 523/300 |
| 5,412,076 A | | 5/1995 | Gagnieu | ..................... | 530/356 |
| 5,527,893 A | | 6/1996 | Burns et al. | .................. | 514/53 |
| 5,786,421 A | | 7/1998 | Rhee et al. | ................. | 525/57.1 |

FOREIGN PATENT DOCUMENTS

| | | |
|---|---|---|
| EP | 0 213 563 | 3/1987 |
| EP | 0 437 095 | 7/1991 |
| EP | 0 686 402 | 12/1995 |
| EP | 0 815 881 | 1/1998 |
| FR | 2 628 634 | 9/1989 |
| FR | 2 759 083 | 8/1998 |
| GB | 1 095 552 | 12/1967 |
| WO | WO 96/08277 | 3/1996 |

OTHER PUBLICATIONS

Nicolas F. et al: "Denatured thiolated collagen. I. Synthesis and characterization" Biomaterials, GB, Elsevier Science Publishers BV., Barking, vol. 18, No. 11, pp. 807–813, XP004063906, ISSN: 0142–9612.

Nicolas F. et al: "Denatured thiolated collagen. II. Cross–linking by oxidation" Biomaterials, GB, Elsevier Science Publishers BV., Barking, vol. 18, No. 11, pp. 815–821, XP004063907, ISSN: 0142–9612.

Greene : "Protecting Groups in Organic Chemistry", Wiley, 1975.

"Chemistry of protein conjugation and cross–linking" S. S. Wong, Boca raton, CRC Press, 1993, Chap. 2.

Techniques in Protein Modification, R.L. Lundblad, CRC Press Chapters 10–14 (not dated).

* cited by examiner

Primary Examiner—Jeffrey Edwin Russel
(74) Attorney, Agent, or Firm—Finnegan, Henderson, Farabow, Garrett & Dunner, L.L.P.

(57) ABSTRACT

The aim of the invention is to provide a modified collagen peptide for preventing post-operative adhesions that is non-toxic, economic, in addition to being easy to obtain, sterilize, manipulate and implement, having controlled biodegradability and presenting a sufficiently strong initial mechanical resistance in situ (cohesion). This is achieved in the case of the modified collagen peptide for preventing post-operative adhesions according to the invention which is characterized in that it comprises at least one collagen peptide that is modified by grafting thiol functions that are free or substituted, cross-linkable and/or at least partly cross-linked, whereby the thiol functions are provided by mercaptoamine radicals that are exclusively grafted on the aspartic and glutamic acids of the collagen chains by means of amide bonds. The modified collagen peptide can exist in the form of a homogeneous or composite film, as a gel or in as a liquid which can be applied and cross-linked per se as on in vivo tissue.

27 Claims, No Drawings

CROSS-LINKED COLLAGENIC PEPTIDE FOR PREVENTING POST-SURGICAL ADHESIONS

The domain of the invention is that of biocompatible, bioresorbable medical or surgical biomaterials which can be used in the prevention of post-operative adhesions, more particularly after intraperitoneal and pelvic surgical interventions.

The invention relates to a means, more especially, but not in a limiting way, a film, a gel or a liquid (applicable e.g. by pulverization), for preventing these post-surgical adhesions, consisting of a chemically modified specific collagenic peptide which is crosslinked in situ or used in the crosslinked state.

The invention also relates to a process for producing, inter alia, the abovementioned means.

One of the major problems encountered in surgery, in particular digestive, abdominal and gynecological surgery, is related to the formation of post-surgical adhesions (abnormal association between two surfaces or segments of tissues which are normally separated) which are the result of an inflammatory and/or cicatricial activity automatically generated subsequent to a tissue trauma engendered by the invention. Such delocalized adhesions can have unfortunate repercussions. Thus, in abdominal surgery, these adhesions may lead to obstructions. In gynecological surgery, post-operative pelvic lesions are one of the recognized causes of the lack of effectiveness of surgical treatment for sterility.

In order to attempt to remedy this problem, chemical and/or therapeutic approaches have been proposed.

The chemical approach consists in applying to surgical wounds chemical treatment agents capable of curbing the physiological phenomena of inflammation and cicatrization which cause the adhesions. These treatment agents are enzymes such as fibrinolysin and papase, or products such as phenylbutazone, prednisolone, polyvinylpyrrolidone or dextrans.

The physical approach consists in isolating the surgical wound from the neighboring tissue by intercalating a physical barrier, which may be a film or a dressing which is nonfibrous or fibrous, woven or nonwoven, or in the form of a gel. This physical barrier prevents adhesion during the cicatrization. However, as soon as the latter is no longer taking place and, therefore, the risks of adhesion are nonexistent, this physical barrier represents nothing other than a useless, or even bothersome, not to say dangerous in certain cases, foreign body.

Hence, it ensues that the known anti-adhesive means made of polymer materials of the polytetrafluoroethylene or silicon type which, although being tried and trusted in terms of anti-adhesion, nonetheless remain nonbiodegradable and must therefore be removed during a second surgical operation. This practice which is doubly traumatizing for the patient has the other drawback of shifting the problem of post-surgical adhesion from one tissue region to another which is lesioned during the second operation (laparotomy).

Thus, in order to move on from this, attempts have been made to develop means for preventing post-operative surgical adhesions, consisting of materials which are biodegradable (or bioresorbable) at the end of the cicatrization, as soon as their function as a barrier has been fulfilled and that no risk of adhesion remains. Some researches, in the knowledge of the presumed biodegradability and biocompatibility properties of natural polymers and of derivatives thereof, have proposed using collagenic peptides (collagen, gelatin), polysaccharides (cellulose-starch and derivatives) and mucopolysaccharides, inter alia, as a constituent material of implants or of surgical prostheses, and in particular of post-surgical anti-adhesion barriers.

The company Johnson & Johnson Products Inc, has developed a bioresorbable material based on oxidized regenerated cellulose, which can be used as a post-operative anti-adhesion barrier and is in the form of cloth with a density of 8 to 15 $Mg/cm^2$ and a porosity of 10 to 20% (EP-A-0 213 563). JOHNSON & JOHNSON has also developed a process for preparing neutralized oxidized cellulose, the integrity and tensile strength of which are preserved, with a view to uses, in particular as a means for preventing post-surgical adhesions (EP-A-0 437 095). As an extension to that, this company has also developed a multilayer film made of oxidized cellulose and cellulose, which can be used as an anti-adhesion barrier or as a dressing (EP-A-0 815 881).

In patents U.S. Pat. No. 5,017,229 and U.S. Pat. No. 5,527,893, the inventors, BURNS et al. of the company GENZYME CORPORATION, describe a barrier for preventing post-surgical adhesions, consisting of a polyanionic polysaccharide, namely carboxynethylcellulose, combined with hyaluronic acid so as to form a gel.

In general, uses for collagenic materials as surgical films have been known for a long time. Thus, British patent GB-A-1 095 552 from 1964 describes a collagen film made from multiple nonwoven filaments.

French patent FR-A-2 628 634 describes a visceral surgery patch prepared using a biomaterial made from two superposed and tightly associated layers of collagen, namely an adhesive porous layer of fibrous collagen and a film of collagen and/or of gelatin. The aim of this patch is to allow good cicatrization of the viscera. It is a dressing intended to temporarily replace the visceral wall to be reconstituted. It is presented as being entirely biodegradable and as being capable of producing an excellent effect of containment and of hemostasis. It does not, in this case, specifically involve use for preventing post-surgical adhesions.

PCT patent application WO 96/08277 relates to the use of collagenic membranes as a prosthesis for peritoneal regeneration. The collagenic material under consideration is a gel of optionally crosslinked collagen, which is transparent and biocompatible, which can be sutured or stapled, and which is bioresorbable. The collagen used is a collagen with or without telopeptides, optionally associated with a glycosaminoglycan. It should be noted that the crosslinking agent optionally used is a reactive chemical compound (glutaraldehyde, diphenylphosphoryl azide, carbodiimide) which is not neutral in terms of toxicity.

In patent FR-A-2 628 634, the patch is formed by two superposed and tightly associated layers of collagen. The first layer is made from fibrous collagen which confers a porous and adhesive nature on it. The second layer is obtained by adhering a film of collagen or of gelatin onto the first layer of fibrous collagen. According to the inventors of PCT patent WO 96/08277, this patch has a relatively low mechanical resistance. Document FR-A-2 628 634 makes no mention of the prevention of post-surgical adhesions.

European patent application EP-A-0 686 402 discloses a collagenic membrane for preventing post-surgical adhesions, comprising a collagen-based support covered with a layer of gelatin which is not mixed with the support. This membrane is preferably provided in lyophilized form. The collagen used may be crosslinked using diphenylphosphoryl azide (DPPA). Once again, this type of crosslinked collagen is not a sound choice because of the problems of toxicity of which it is the underlying cause.

French patent application FR-A-2 759 083 describes a collagenic material which can be used in particular for preventing post-surgical adhesions. According to the inventors, this collagenic material is biocompatible, nontoxic, potentially adhesive and biodegradable in less than a week. This collagenic material comprises collagen which is modified by oxidative cleavage and heating above 37° C. and which is crosslinked in the presence of at least one macromolecular hydrophilic additive which is chemically nonreactive with respect to collagen. The hydrophilic agent is, for example, polyethylene glycol or a polysaccharide such as starch, dextran or cellulose.

It emerges from this review of the prior art that none of the biodegradable materials, in particular the cellulose or collagenic materials, used to date in the prevention of post-surgical adhesions are satisfactory, in particular for the reasons stated hereinafter.

Some may have residual toxicity, given their method of chemical crosslinking, for example using aldehydes.

The biodegradability is not sufficiently controlled to be considered compatible with maintaining their function of a physical barrier between tissues, during and only during the period of time for cicatrization during which the risks of surgical adhesion exists.

Some have a very low initial mechanical resistance.

With regard to collagenic materials, they cannot be produced in the form of solutions which can be filtered over filters with a porosity which is sufficiently low to allow the retention of biological contaminants (sterilization).

One of the essential objectives of the present invention is to provide a means, based on collagen, for preventing post-surgical adhesions, this means needing to satisfy the specifications which remedy the abovementioned drawbacks of the materials of the prior art.

Another essential objective of the invention is to provide a means for preventing post-surgical adhesions, comprising a collagenic material which can be used as a support for one or more chemical agents for combating post-surgical adhesions.

Another essential objective of the invention is to provide a means for preventing post-surgical adhesions, comprising a modified and crosslinked collagen which can be manufactured in the form of a film or of a membrane. This film or membrane may consist of a composite material comprising, firstly, chemically modified and crosslinked collagen which satisfies the abovementioned requirements and, secondly, a reinforcement material which may or may not be woven, which is preferably biodegradable and which may or may not be collagenic in nature.

Another essential objective of the invention is to provide a means for preventing post-surgical adhesions, consisting of a liquid form (e.g. sprayable liquid or gel) with a suitable viscosity comprising modified collagen which is at least partly non-crosslinked and which is crosslinkable in situ on the biological tissues.

Another essential objective of the invention is to provide a means for preventing post-surgical adhesions, which is economical and easy to produce, to handle and to use.

Having set all these objectives, the inventors carried out long and laborious investigations and experiments, at the end of which they were able to develop, entirely surprisingly and unexpectedly, a novel chemically modified collagenic peptide which is crosslinkable and/or crosslinked via disulfide bridges attached to the carboxylic units of the aspartic and glutamic acids of the collagenic chains by amide bonds. This novel crosslinkable/crosslinked collagen has proved to be particularly suitable as an essential constituent element of a means—de facto, also novel itself—for preventing post-surgical adhesions.

Hence, it ensues that the present invention satisfies the objectives targeted above, inter alia, by providing a means for preventing post-surgical adhesions, characterized in that it comprises at least; one collagenic peptide which is modified by grafting free or substituted thiol functions, which is crosslinkable and/or at least partly crosslinked and the thiol functions of which are provided by mercaptoamino residues exclusively grafted onto the aspartic and glutamic acids of the collagenic chains, via amide bonds.

For the purposes of the present invention, the term "collagenic peptide" denotes in particular collagen with telopeptides (native collagen) or without telopeptides, denatured collagen and gelatin.

The collagenic peptides selected, in accordance with the invention, has the particularity that the crosslinking functionalities are borne exclusively by carboxyl residues of the aspartic and glutamic acids of the collagenic chain. This confers on it properties which are unexpected but advantageous in terms of mechanics, of solubility in aqueous medium, of adhesion and of biology (biodegradation).

This chemically modified collagenic peptide may exist in at least three different forms:

A. precursor with substituted thiol functions,

B. crosslinkable precursor with free thiol functions,

C. —S—S— crosslinked form.

The B form can be obtained from A and the C form can be obtained from the B form.

The means for preventing adhesions according to the invention comprises at least one of the A, B or C forms. It is clear that the A and B forms correspond more especially to the means in the state for the packaging and storage thereof before application to the site at which it is intended to express its anti-adhesion function. Furthermore, it is in the crosslinked C form that said means is most able to express this function.

In the crosslinked C form, the chemically modified collagenic peptide which is a constituent element of the means according to the invention may have high density of disulfide bridges which provide it with excellent stability and also good elastic properties and high mechanical resistance. Another advantage of this judicially selected collagenic peptide comes from the fact that its degree of crosslinking may be controllable. Finally, the chemical modification of the collagenic peptide under consideration by grafting mercaptoamino residues is harmless or relatively harmless in terms of its biocompatibility.

The use of this at least partly crosslinked collagenic peptide (C) as a means for preventing post-surgical adhesions is entirely judicious and original. It makes it possible to have a novel anti-adhesion means which forms a barrier between the tissues in an entirely effective way, while being completely tolerated by the body of the patient. Its bioresorbability may be regulated such that the means conserves its barrier effect function for the period of time necessary for the cicatrization.

The means according to the invention may give rise to various manufactured products of the film, gel, sprayable liquid, dressing, gauze, compress, plaster, etc. type.

Another advantageous arrangement of this means is a result of the fact that the intermediate A and B forms may be provided in the form of a solution which can be filtered over meshes of less than 0.22 microns. This makes it possible to rapidly and easily perform a sterilization, which is essential for products intended to be implanted in vivo.

Advantageously, at least some of the modified collagenic peptide which is a constituent of the means according to the invention is in the form of a precursor A onto which are grafted mercaptoamino residues bearing substituted thiol functions, at least some of these mercaptoamino residues corresponding to the following general formula (I):

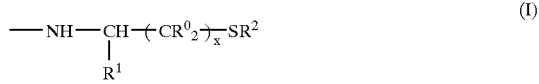

in which:
x=1 or 2,
$R^0$=H or $CH_3$,
$R^2$ represents H or $COOR^3$ with $R^3$ corresponding to a hydrocarbon-based radical of the aliphatic, aromatic or alicyclic type, preferably of the alkyl, alkenyl, aryl, aralkyl, alkylaryl, aralkenyl or alkenylaryl type, and even more preferably of the methyl or ethyl type;
$R^2$ is an aliphatic and/or alicyclic and/or aromatic radical, preferably an alkyl or an acyl, optionally a sulfur-containing and/or amino-alkyl or acyl, and even more preferably $R^2$ corresponds to the following formula (II):

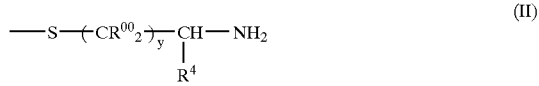

with y, $R^{00}$ and $R^4$ corresponding to the same definition as that given in the legend in formula (I) for x, $R^0$ and $R^1$.

In practice, the mercaptoamino residues grafted onto the A form of the collagenic peptide are chosen from the group of the following radicals:

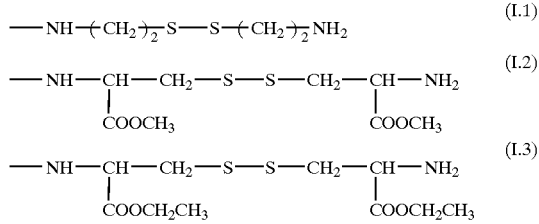

To transform the precursor A in which $R^2$ corresponds to: —S-hydrocarbon-based radical (substituted thiols) into the thiol-type intermediate crosslinkable precursor B, a reduction is carried out using known reducing agents such as mercaptans (mercaptoethanol, mercaptoacetic acid, mercaptoethylamine, benzyl-mercaptan, thiocresol, dithiothreitol, etc.) and/or reducing salts ($NaBH_4$, $Na_2SO_3$, etc.) and/or organic reducing agents (phosphine). Thus, according to a preferred characteristic of the invention, at least some of the modified collagenic peptide is in a thiol-type intermediate crosslinkable precursor form B, onto which are grafted mercaptoamino residues, at least some of which correspond to the general formula (I) given above and in which the substituent $R^2$ corresponds to hydrogen and in which $R^3$ may represent hydrogen or a salt ($Na^+$, $K^+$, $Li^+$), besides the hydrocarbon-based groups as defined above in the legend of formula (I), inasmuch as the ester is deprotected.

As regards the thiol-type crosslinkable precursors B corresponding to the formula (I) in which $R^2$=H, the transformation into the crosslinked collagenic peptide C (crosslinking) takes place by oxidation of the thiols to disulfide bridges. This makes it possible to produce a three-dimensional collagenic network which is insoluble in physiological media and soluble in reducing media capable of reducing the disulfide bridges. This oxidation may take place spontaneously in the presence of the oxygen in the air, advantageously in weakly basic medium, and optionally in the presence of auxiliary oxidizing agents such as hydrogen peroxide or iodine-containing derivatives (iodine solution, betadine).

Thus, according to a preferred mode of the means according to the invention, at least some of the modified collagenic peptide is in a crosslinked form C comprising collagenic chains attached to one another by disulfide bridges, the constituent sulfur atoms of which belong to mercaptoamino residues exclusively grafted onto the aspartic and glutamic acids of the collagenic chains, via amide bonds.

Even more preferably, the collagenic peptide in the C form is obtained from the collagenic peptide B.

These crosslinked collagenic peptides C have a level of crosslinking which can be controlled by adjusting the degree of substitution of the carboxylic units of the aspartic and glutamic acid residues of the collagenic chains. There is thus a certain margin for maneuver for choosing the mechanical quality of the materials suitable for the intended application.

The disulfide bridges of these crosslinked collagenic peptides C may be reduced using suitable reducing agents, examples of which have been given above.

According to a variant of the invention, the collagenic peptide A, the crosslinkable collagenic peptide B and/or the at least partly crosslinked collagenic peptide C, which is a constituent of the means claimed, also carries grafts G attached to at least some of the free amine units of the collagenic chain, via amide bonds, G being an acyl comprising a hydrocarbon-based entity, EXCLUDING mercaptoamino residues, in particular those as defined above, optionally containing hetero atoms (advantageously O and/or N), preferably chosen from alkyls and/or alkenyls and/or alicyclics and/or aromatics, and even more preferably from the groups comprising an alkyl chain, optionally unsaturated and comprising from 1 to 22 carbon atoms or corresponding to the following formula (III):

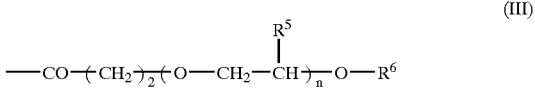

with:
$R^5$=H or $CH_3$;
$R^6$=H, or a linear or branched alkyl radical, and preferably a methyl;
z=0, 1 or 2 and n>0.

This additional functionalization on the amine sites of the lysines may confer on the modified collagenic peptides a further capacity for crosslinking or alternatively a hydrophilic or hydrophobic, or even a surfactant, nature. It is also conceivable for this functionalization to have therapeutic purposes via the anchoring of an active principle, which may be, for example, in the application concerned, one or more chemical agents for anti-adhesion treatment.

According to an advantageous characteristic of the invention, this graft G, which is attached to the free amines of the collagenic chain of the crosslinked, collagenic peptide, modifies the hydrophilic/hydrophobic nature of the product, which makes it possible to modulate the properties of swelling, of mechanical resistance and of degradation kinetics.

With regard to the production of a collagenic precursor A carrying mercaptoamino residues (I), it consists essentially in reacting the collagenic peptide in solution with at least one precursor of a mercaptoamino residue, the thiol function and the possible carboxylic function of which are blocked, in the presence of at least one grafting agent, preferably chosen from the group of products which activate carboxylic groups, preferably from carbodiimides.

The production conditions are chosen such that the grafting of the mercaptoamino residue takes place on the free carboxylic acid units of the aspartic and glutamic acid residues of the collagenic chain.

To this end, the precursor to be grafted should have the free amine function capable of reacting with the collagenic COOHs so as to form an amide bond. This precursor is, for example, a cysteine, a homocysteine or a cysteamine, the thiol function and the possible carboxylic acid function of which is(are) correctly protected. An effective means for protecting the thiol function is to choose, as a cysteine-based residue to be grafted, cystine, homocystine or cystamine, all three of which comprise a disulfide bridge which stabilizes the mercapto function. As other means of protecting the latter, any conventional function for protecting thiols which is known in the prior art may be chosen (see, for example "Greene: *Protecting Groups in Organic Chemistry*, WILEY, 1975").

As far as the COOH functions are concerned, they may be protected using a protective group or any other organic function capable of introducing any advantageous property (PEGS, hydrophobic, hydrophilic or charged groups).

According to an advantageous arrangement of the invention, the precursor of the mercaptoamino residue to be grafted corresponds to a formula (IV) which corresponds to the formula (I) given above and in which the free valency is replaced with a substituent capable of reacting with the carboxylic functions of the aspartic and glutamic acids of the collagenic chain, this substituent preferably being hydrogen, in such a way that the reactive function is a primary amine. The most especially preferred precursors of formula (IV) are cystamine (I.1), cystine dimethyl ester (I.2) and cystine diethyl ester (I.3), all three of which comprise a disulfide bridge which protects the mercapto function.

In practice, the grafting of the mercaptoamino residue is carried out by dissolving the collagenic peptide and then the precursor of the mercaptoamino residue to be grafted in a suitable solvent. It may, for example, be water (preferably) or an organic solvent, such as dimethyl sulfoxide (DMSO, N-methylpyrrolidone (NMP) or others. The precursor of the mercaptoamino residue to be grafted is always present in large excess in order to avoid the activated collagen reacting with the amines contained within its own backbone.

A coupling agent, such as a carbodiimide, is then added to the reaction solution and the grafting is allowed to take place by maintaining the medium with stirring for a few hours at room temperature.

These collagenic peptides A substituted with mercaptoamino residues which are precursors of the crosslinkable thiol residues are novel intermediate products which are stable and soluble in water. They may be isolated and purified, for example by dialysis, diafiltration and then lyophilization or by precipitation in organic medium and then by drying.

The thiol-type intermediate collagenic precursors B, in which $R^2$=H, may be obtained using a process consisting essentially in deprotecting (transformation to thiols) the mercapto functions of the mercaptoamino residues grafted onto the modified collagenic peptides A as indicated above.

When the protection or masking of the mercapto functions is provided by a disulfide bridge (i.e. when the precursors of the grafts are, for example, cystamine or cystine), the thiol function is regenerated by reduction. The latter may be carried out using reducing agents, such as mercaptans (mercaptoethanol, mercaptoacetic acid, mercaptoethylamine, benzylmercaptan, thiolcresol, dithiothreitol, etc.), and/or reducing salts ($NaBH_4$, $Na_2SO_3$, etc.) and/or organic reducing agents (phosphine).

Advantageously, the protecting disulfide bridge is reduced in basic aqueous medium using dithiothreitol. After this step, the thiol-containing collagen obtained is purified by dialysis/diafiltration and may be isolated, e.g. by lyophilization.

As already emerges from the above, the crosslinked collagenic peptides C are prepared by oxidation of the thiol functions of the crosslinkable modified collagenic peptide B, so as to form interchain disulfide bridges.

As regards the functionalization of the abovementioned collagenic peptides, with grafts G, the nature of which is different from that of the grafts of formula (I) (optionally hydrogenated) attached to the COOH of the aspartic and glutamic acids, it consists essentially:

in carrying out an acylation of at least some of the free amine functions of the collagenic chain, so as to attach to the latter grafts G comprising a hydrocarbon-based entity, EXCLUDING mercaptoamino residues, in particular those as defined above, this entity optionally containing hetero atoms (advantageously O and/or N), preferably chosen from alkyls and/or alkenyls and/or alicyclics and/or aromatics, and even more preferably from the groups comprising an alkyl chain, optionally unsaturated or corresponding to the following formula (III):

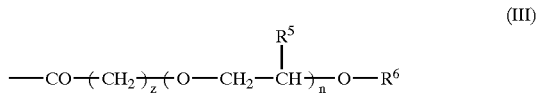

(III)

with:
$R^5$=H or $CH_3$;
$R^6$=H, or a linear or branched alkyl radical, and preferably a methyl;
z=0, 1 or 2 and n>0;

in reacting the collagenic peptide in solution with at least one precursor of a mercaptoamino residue, the thiol function and the possible carboxylic function of which are blocked, in the presence of at least one grafting agent, preferably chosen from the group comprising the compounds capable of activating carboxylic groups, preferably carbodiimides.

In order to be able, to react with the free amine functions of the lysines of the collagenic chain by acylation, the precursors of the grafts G must comprise at least one activatable carboxylic acid function.

The reactions for acylation and for coupling of amine functions with carboxylic sites belonging to proteins are known to those skilled in the art in the field of protein biochemistry. For further details in this regard, reference will in particular be made to the following works:

"*Techniques in protein chemistry*" R. L. LUNDBLAD chap. 10–14,

"*Chemistry of protein conjugation and cross-linking*" S. S. WONG, Boca raton, CRC Press, 1993, chap. 2.

After this description of the product which is an essential constituent of the means according to the invention, the remaining text will provide details regarding the physical characteristics, the method for preparing and the method for using said means for preventing post-surgical adhesions.

In accordance with a first embodiment of the means according to the invention, this means is in the form of a film. For the purposes of the present invention, the term "film", is intended to mean a material in the form of a sheet, the surface area of which is substantially larger than the thickness.

According to a second embodiment of the means according to the invention, this means is in the form of a fibrous substance, which is woven or nonwoven, preferably woven, and even more preferably oven with knitted stitches.

By way of examples of means according to the invention consisting of fibrous collagenic materials, mention may be made of woven and/or knitted and/or braided sheets or felts and mats.

According to a third embodiment of the means according to the invention, this means may be in the form of a film (or of a sheet) made of a nonhomogeneous composite material, in which a reinforcement made of a biodegradable polymer, which may or may not be collagenic in nature, is included in the matrix consisting of the collagenic peptide defined above. The polymer constituting the reinforcement may be collagenic peptide selected in accordance with the invention, nonmodified collagen or other biocompatible and biodegradable polymers, such as α-hydroxycarboxylic acid polymers (e.g. poly(lactic acid) and/or poly(glycolic acid)), celluloses or starches, which may or may not be modified. The possibility of these inclusion polymers being synthetic or natural polymers which are nonbiodegradable but biocompatible (e.g. silicones, etc.) should not be excluded.

The reinforcement material may be in various physical forms, e.g. particulate or fibrous fillers, mats, felts, materials which are woven, knitted, braided, etc. In practice, the means according to the invention may, for example, consist of a composite film comprising a matrix made of a collagenic peptide which is at least partially in a crosslinked form C, as defined above, and a reinforcement material consisting of a cloth or a mat comprising fibers of α-hydroxycarboxylic acid polymers (poly(lactic acid) and/or poly(glycolic acid)).

This fibrous reinforcement material is, for example, the same shape as the matrix (for example rectangular), while at the same time having slightly smaller dimensions.

According to a particular embodiment, the means according to the invention may be in the form of a film comprising a fibrous reinforcement over only part of its surface. In practice, the central region of the fibrous reinforcement material may be hollowed out.

In any event, it is advantageous for the fibrous reinforcement to be present over at least part of the edges of the composite film, so as to provide a zone suitable for accepting suture threads.

Using the crosslinked collagenic peptide in the form of a film (optionally composite film), it is possible to manufacture, in accordance with the invention, membranes which can be sutured and which are effective in the prevention of post-surgical adhesions.

Preferably, the means according to the invention is a composite film in which the matrix is made of crosslinked collagenic peptide and in which the reinforcement material is in the form of fibrous material, which is woven or nonwoven, preferably woven, and even more preferably woven with knitted stitches, this reinforcement material also being advantageously chosen from α-hydroxycarboxylic acid (co)polymers, preferably poly(lactic acid)s and/or poly(glycolic acid)s.

However, it is entirely conceivable, in accordance with the invention, that the means for preventing post-surgical adhesions should be placed (applied) and/or implanted on the site at which it is intended to act as a barrier, not in a solid form, but in a liquid (fluid or viscous) form. Hence, it ensues that, according to a fourth embodiment of the means of the invention, this means is in a nonsolid form which is crosslinkable and/or at least partly crosslinked and which can be applied and/or implanted onto and/or into a support.

In this case, the nonsolid form is, for example, a solution of crosslinkable collagenic peptide (precursor B). It is applied directly onto a support (for example biological tissues) and is then subjected to crosslinking which allows it to harden into a gel. The crosslinking may be produced in situ by the action of a medically accepted chemical oxidizing agent, via the oxygen in the air or via any other oxidation means which can be easily used during a surgical operation (UV, electrocoagulation, etc.).

In this fourth embodiment, the nonsolid form of the collagenic peptide, which is included in the means according to the invention, may advantageously be in the form of a liquid which can be gelled, in particular by oxidation, and/or physically in the form of a gel intended to be applied thus onto a support (e.g. biological tissues) where it will exert its anti-adhesion action. In this nonsolid gelled form, the collagenic peptide may, optionally but not necessarily, be partially in the crosslinked form. However, it goes without saying that, in this hypothesis, the proportions of crosslinked collagenic peptide C compared to its noncrosslinked precursor B are chosen such that the solid state is never reached.

The nonsolid (i.e. liquid) form of the collagenic peptide precursor, namely e.g. a liquid collagenic solution, may be applied directly using a tool, preferably a syringe or a spray. In this way, according to an advantageous variant of the fourth embodiment of the means according to the invention, this means comprises at least one tool, preferably a syringe or a spray, for storing and applying into and/or onto a support, the nonsolid form of the crosslinkable and/or at least partly crosslinked collagenic peptide, as defined above.

When the means according to the invention is a spray of the modified collagenic peptide in liquid form, the spraying may take place via a pump/nozzle system and/or via a gaseous propellant.

The support may be understood, herein, to be biological tissues (for example animal tissues), the dressing and/or treating of which, e.g. in vivo, with a view to preventing post-surgical adhesions, is desired.

Optionally, the rheological properties of the collagenic solution may be adjusted by adding a natural or synthetic polymer which is biocompatible, preferably biodegradable (such as, for example, polysaccharides, glycosaminoglycans, proteins or glycoproteins, ethoxylated polymers such as polyethylene glycol, etc.).

When a chemical agent is used to crosslink the solution, it is advantageously chosen from the oxidizing agents conventionally used in medicine, such as for example, hydrogen peroxide.

It is possible to associate with this fourth embodiment of the means of the invention (collagenic peptide liquid/gel), a process for implementing a means for preventing post-surgical adhesions of living tissues, characterized in that it consists, essentially:

in using a collagenic fluid, e.g. a solution, of the collagenic peptide of the type defined above;

in applying this fluid onto biological tissues, for example using a syringe or a spray;

and in bringing about crosslinking of the collagenic fluid in situ, for example using a biocompatible oxidizing agent (e.g. oxygen in the air, $H_2O_2$, etc.).

According to a first embodiment of this process, the mixing of the oxidizing agent and of the fluid, for example the collagenic solution, may be carried out before it is deposited. In this case, the solution applied is already partially crosslinked at the moment it is deposited. The homogeneity of the solution/oxidizing agent mixture can be ensured with an application device, such as a double-syringe system equipped with a mixing head (device similar to that used for fibrin-based biological adhesives), a double spray equipped with a mixing nozzle or any other device for ensuring a homogeneous mixture.

According to a second embodiment of this process, the application is performed in two steps. Preferably, the fluid, for example the liquid collagenic solution, is first deposited and then the oxidizing solution is deposited. However, a reverse order of addition may also be used.

According to a fifth embodiment of the means according to the invention, the latter is in the form of a composite or homogeneous block which is not comparable to a film.

According to another of its aspects, the present invention relates to a process for preparing the means for preventing post-surgical adhesions as described above.

In accordance with a first pathway of implementation corresponding to the preparation of the solid forms (for example films or homogeneous blocks or composites: 1st, 3rd and 5th embodiments), the process comprises the following essential steps:

1. preparing a solution, preferably an aqueous solution, of crosslinkable precursor of modified collagenic peptide;
2. optionally filtering this solution so as to extract therefrom the elements which are greater than or equal to 0.8 $\mu$m, preferably greater than or equal to 0.45 $\mu$m, and even more preferably greater than or equal to 0.2 $\mu$m in size;
3. molding the filtrate in the intended configuration for the means for preventing post-surgical adhesions to be prepared;
4. optionally gelling the molded solution, in a maturation phase, by decreasing its temperature below its gelling temperature;
5. optionally eliminating the solvent, preferably by evaporation;
6. bringing about the crosslinking, preferably by oxidation;
7. where appropriate, eliminating, with successive washes, the oxidizing agent possibly used;
8. optionally impregnating the material which is crosslinked or, which is in the process of being crosslinked, using a solution of at least one plasticizer (for example: glycerol, low molecular weight polyethylene glycol);
9. optionally drying the crosslinked material;
10. optionally cutting the material to the size for use;
11. optionally sterilizing the crosslinked material by radiation.

One of the advantages of the preparation process according to the invention comes from the fact that it can be carried out simply, sterilely and economically.

The dissolving step 1 is performed, for example, using a solvent consisting of sterile water, at a temperature of between 20 and 50° C. and a pH of between 6 and 8. According to a preferred characteristic of this first pathway of the process according to the invention, the solution prepared in step 1 has a titer in terms of crosslinkable precursor of the collagenic peptide of greater than or equal to 1%, and preferably between 1 and 15%.

The filtration step 2, which is optional but nevertheless preferred, is a means for purifying or even sterilizing the solution prepared in step 1. Due to the quality of water-solubility of the precursor of the crosslinked collagenic peptide, selected according to the invention, it is possible to filter the precursor solutions over filters with a porosity of less than 0.8 microns, preferably $\geq$0.45 microns, and even more preferably of about 0.2 microns. This ability to be able to sterilize by filtration is a considerable asset in industrial terms.

Step 3 consists in molding the filtered solution so as to produce a crosslinked object of controlled shape and controlled size. For implementing step 3, it is possible, for example, to pour the filtered solution into molds, preferably sterile molds. According to a variant of this step, it is also possible to deposit the filtered solution on a sterile flat support, by coating. According to another variant, the molding can be carried out by extruding the solution through a die of a shape which is suitable for the intended means, for example rectangular. In the latter case, some solidification must occur during the extrusion in order for the latter to be possible.

The optional, but nevertheless preferred, maturation of step 4 (or physical gelling) of the solution consists in leaving the molded solution to stand for several hours, or even several days, at a temperature lower than its gelling temperature or gel/solid transition temperature, which may, for example, be between 20 and 30° C., in the case of an aqueous solution of collagenic peptide.

The elimination of the solvent, preferably water, according to step 5, is an optional phase which can be carried out during or after the gelling, preferably after. It may preferably be evaporation at a given temperature in the optional presence of desiccating agents.

The crosslinking according to step 6 is carried out on molded, optionally gelled, articles which are advantageously in dry form. The crosslinking consists in oxidizing the thiol-type precursor of the collagenic peptide using an oxidizing agent such as iodine or $H_2O_2$. After several minutes of contact with the oxidizing agent, it is preferable to carry out (step 7) successive washes of the articles thus fashioned. The latter may then be transformed, as desired, into various means for preventing post-surgical adhesions.

At the end of these steps, the crosslinked materials produced are in a hydrated state. They may optionally be impregnated (step 8) using a plasticizing material commonly used for molding collagenic materials (glycerol, low molecular weight polyethylene glycol). The plasticizing material may also be introduced as early as step 1 for preparing the solution.

Finally, the collagenic materials, which may or may not be loaded with plasticizer(s), may be dried (step 9).

Although this process may be carried out using sterile means and optionally comprise a sterilizing filtration step, an additional sterilization step (step 10), for example with $\beta$-radiation, may be envisioned.

The articles produced, for example the films, are stable in the dry state over long periods and can be manipulated after rehydration in any suitable aqueous liquid.

According to a variant of this first pathway for preparing the means of the invention, it is possible, for example, to include a reinforcement during step 3, either by pouring the filtered collagen solution onto the reinforcement deposited in the mold or onto the support, or by depositing the reinforcement onto the solution which has already been poured and optionally gelled. In the latter case, a second layer of collagenic solution may again be deposited.

Depending on the method for introducing the reinforcement, a membrane having a "collagenic peptide" face and a "reinforcement" face or a "collagenic peptide/reinforcement/collagenic peptidel" trilayer membrane may thus be produced. These examples are not limiting and other variants of the process for producing composite materials from the collagenic peptide defined above may be envisioned.

In accordance with a pathway of implementation, corresponding to the nonsolid (liquid) forms of the means according to the invention, the process comprises the following essential steps:

1. preparing a solution, preferably an aqueous solution, of crosslinkable precursor of modified collagenic peptide;
2. optionally filtering this solution so as to extract therefrom the elements which are greater than or equal to 0.8 $\mu$m, preferably greater than or equal to 0.45 $\mu$m, and even more preferably greater than or equal to 0.22 $\mu$m in size;
3. optionally concentrating the solution;
4. packaging the solution sterilely under an inert atmosphere.

According to a preferred characteristic of this second pathway of the process according to the invention, the solution prepared in step 1 has a titer with regard to the crosslinkable precursor of the collagenic peptide of greater than or equal to 1%, and preferably between 1 and 15%, and a pH between 4 and 10, and preferably between 6 and 8.

During step 1, it is possible to add, to the solution, natural or synthetic, biocompatible polymers or small biocompatible molecules which can modify the rheology of the solution and delay the gelling of the material (for example urea). In practice, the amounts of polymers incorporated are such that said polymers represent, in the final crosslinked form of the prevention means, between 1 and 50% of the total solids, and preferably between 1 and 20%. Step 1 is preferably carried out under sterile conditions, using sterile polymers (collagenic peptide precursors and optional additive polymers).

The filtration step 2 is optional and is not necessary if step 1 has been carried out under sterile conditions. When filtration takes place, it is carried out at a temperature greater than 35° C. and preferably between 40 and 50° C.

The concentrating step 3 is optional. It is carried out sterilely by partial evaporation of the solvent so as to produce concentrated solutions with a titer with regard to the crosslinkable precursor of the collagenic peptide of between 5 and 30%, and preferably between 10 and 20%.

The packaging step 4 is carried out in a sterile manner under an inert atmosphere (nitrogen or argon). The solution is packaged in a container which may be the definitive form for application (syringe or spray) or a storage bottle.

It should be noted that, at room temperature, the liquid form of the means may be in gelled form. This gel, which is characteristic of collagenic products, may be refluidized after stirring for a few seconds at 40° C.

This solution may then be crosslinked by oxidation in a chemical gel.

According to a third pathway of implementation, which combines the first two, the packaged solution produced at the end of step 4 of the second pathway is applied onto a support and crosslinking is brought about, preferably using a biocompatible oxidizing agent.

Another aspect of the invention covers the use of the means described above (film, liquid/gel based on the collagen peptide) for preventing post-operative adhesions.

The means of the invention have the advantage that they can be easily put in place during the surgical act. This depends on the physical and chemical form of the means (crosslinked membrane or noncrosslinked liquid form).

The membranes can be extemporaneously cut to the size of the lesioned zone to be protected. The membranes are applied between the biological tissues likely to give surgical adhesions. They can be put in place in dry form or can be hydrated, just before being put in place, in physiological saline. They can be maintained in place with sutures or by prior application of a surgical adhesive (based on fibrin or on collagenic materials).

According to a variant of use, the membrane may be rolled up on itself and introduced using a trocar, according to a conventional technique of surgery under celioscopy.

As regards the nonsolid (liquid/gel) means for preventing post-surgical adhesions, they may be applied, in particular, in two manners which are defined below.

According to a first manner of application, the liquid form may be deposited directly onto the lesioned tissues using a syringe, a spray or any other application device. Depending on the composition of the formulation and the method of application, it may be necessary to reheat the solution to 40° C. for a few seconds before application. The crosslinking is then carried out in situ by applying, in a second step, a surgically acceptable chemical oxidizing agent, such as a diluted solution of hydrogen peroxide. According to variants of this method of application, the oxygen in the air, UV radiation or other sources of energy which can produce oxidation may be used.

According to a second manner of application, the liquid (precursor) form of the noncroselinked collagenic peptide is mixed, just before application, with a chemical oxidizing agent using a suitable device (double syringe equipped with a mixing head, double spray with a mixing nozzle or other mixing device). These two manners of application can also be adjusted in order to be used in celioscopic surgery.

More generally, the invention relates to a process for preventing post-surgical adhesions is characterized in that the packaged solution is applied (e.g. injection or spraying) onto a support (biological tissues) and in that crosslinking is brought about, preferably using a biocompatible oxidizing agent.

It emerges from the description above that the means for preventing post-surgical adhesions according to the invention are, for example:

either solid means, such as optionally composite and/or multilayer films or membranes comprising essentially the at least partially crosslinked collagenic peptide as defined above, or nonsolid (liquid/gel) means comprising the same collagenic material in the noncrosslinked form which is intended to be applied and to be crosslinked in vivo, so as to form, in situ on the site of action (biological tissues), the solid means for preventing post-surgical adhesions.

Due to the nature of their essential constituent material, these means possess, in the crosslinked form, excellent properties of mechanical resistance, of biocompatibility, of bioresorbability and of nontoxicity, excellent properties as a physical barrier to adhesion and excellent properties for the implementation of industrial preparations, these properties being quite superior to those of the means according to the prior art.

The examples which follow will make it possible to fully understand the invention in all its aspects and to reveal all its advantages and its variants of implementation.

EXAMPLES

Part I: Synthesis of the Means

Example 1

Synthesis of a Collagnic Peptide (Form B) in which the Carboxylic Acids are Substituted with Cystein Ethyl Ester (Degree of Substitution Representing 7% Molar of the Amino Acids)

1) Step I: Coupling (Production of Form A):

25 g of atelocollagen (types I+III, extracted from calf hides, 1.3 mmol of COOH/g) are placed in 2.5 l of water and the temperature of the medium is brought to 50° C. with stirring. The 1% w/v solution thus obtained is filtered over 0.22 µm.

Once the temperature has dropped to 30° C., 46.5 g of cystine diethyl ester are added and the pH is adjusted to 4.2. 12 g of 1-(3-dimethylaminopropyl)-3-ethylcarbodiimide hydrochloride are then added and the reaction is allowed to proceed for 2 h at 30° C. with stirring. The reaction medium is concentrated to 5% w/v and dialyzed against water in order to remove the excess of reagents and the by-products of the reaction.

The product obtained is a stable synthetic intermediate. It is a collagenic peptide (form A) in which a fraction of the aspartic and glutamic acids are substituted with cystine diethyl ester. It may be isolated by lyophilization or be reduced in order to produce the corresponding thiol collagen (form B).

2) Step II: Reduction (Production of Form B):

7.6 g of glycine, 5.8 g of 1,4-dithiothreitol and the quantity of 4N NaOH sufficient to attain a pH of 9.0 are added to the modified collagenic peptide in solution at 5% w/v in water obtained in step I. The reaction medium is maintained for three hours with stirring at 35° C. At this stage, the solution is acidified to pH 2 with 6N HCl, dialyzed against 0.012N HCl to remove all traces of reagents and of reaction by-products, and then filtered over 0.22 µm. The product thus purified is isolated by lyophilization. The degree of substitution is measured by assaying with 5,5'-dithiobis-2-nitrobenzoic acid (DTNB), which is a reagent specific for thiol functions. This assay is described in: "Ellman G. L., Tissue sulfhydryl groups, *Archives of Biochemistry and Biophysics*, 1959, 82, 70–77".

[SH]: 0.706 mmol/g of dry product, i.e. 7% molar of substituted amino acids.

The entire synthesis can be carried out aseptically so as to obtain, in fine, the product in the form of a sterile lyophilizate.

Example 2

Preparation of a Film of Modified Collagen Crosslinked with Iodine, for Preventing Post-operative Adhesions Step I:

A 20 g/l solution of collagenic precursor peptide according to example 1 is prepared by dissolving the lyophilizate in sterile water. In this example, 2.0 g of lyophilizate are dissolved in 98 g of sterile water. The solution is stirred in a closed container at 40° C. for 15 min in order to obtain complete dissolution. The pH of the solution is adjusted to 6.5 with 1N sodium hydroxide, at 25° C. The solution is re-stirred at 40° C. for min.

Step 2:

The solution is filtered at 40° C. over membranes with a porosity of 0.45 µm, and then over membranes with a porosity of 0.2 µm. The final filtration takes place over sterile molds (polystyrene Petri dishes may be used).

Step 3:

40.0 g of filtered solution are poured into two 12×12 cm² molds. The molds are re-closed.

Step 4:

The solution is matured, which causes physical gelling, for 24 h at a temperature of 16° C.±1. It is necessary for this temperature to be lower than the gel/sol transition temperature. The maturation is performed in a temperature-controlled chamber, the molds lie on a horizontal plate.

Step 5:

After 24 h, the lids of the molds are removed and the evaporation of the gel solutions takes place over 24 h, at the same temperature in a contained chamber, in the presence of desiccating agents (typically sodium hydroxide chips). After 24 h, the films obtained are dry, clear and smooth.

Step 6:

The dry films are crosslinked at 20° C., by pouring on 30 g of iodine alcoholic solution, obtained by dissolving 1.0 g of iodine in 100 ml of ethanol, and 30 g of water is required to obtain a crosslinked film.

The crosslinked film is removed from the iodinated solution.

Step 7:

Successive washes are performed with 80% ethanol solutions and then with phosphate buffer until total decoloration of the film is obtained.

All the solutions used are sterile.

Step 8:

In this example, no step of impregnation with a plasticizer is carried out.

Step 9:

The film is then left to dry under a laminar-flow hood for 24 h.

The dried film obtained contains a percentage of residual water of about 10%.

Step 10:

The film is then easily cut to the size suitable for the application.

Step 11:

Each piece is packaged individually in a sachet in order to be sterilized by β-radiation.

The films obtained are stable at room temperature for several months. They remain stable and can be manipulated after 24 h in water or in phosphate buffer.

Example 3

Preparation of a Film of Modified Collagen Crosslinked with Hydrogen Peroxide, for Preventing Post-operative Adhesions The process is identical, regardless of the nature of the raw material (collagen) and the level of grafting of the collagenic precursor peptide. Steps 1 to 5 of Example 3 are repeated here until noncrosslinked dry films are obtained.

Step 6':

The dry films are crosslinked at 20° C., by pouring on 30 g of a solution of hydrogen peroxide at 0.3% in a decimolar aqueous ammonium acetate solution.

Step 7:

The crosslinked film is removed and washed successively with 30 g of phosphate buffer, pH 7.4, and 30 g of water.

All the solutions used are sterile.

Step 8:

In this example, no step of impregnation with a plasticizer is carried out.

Step 9:

The film is then left to dry under a laminar-flow hood for 24 h.

The dried film obtained contains a percentage of residual water of about 10%.

Step 10:

The film is then easily cut to the size suitable for the application.

Step 11:

Each piece is individually packaged in a sachet in order to be sterilized by β-radiation.

The films obtained are stable at room temperature. They remain stable and can be manipulated after 24 h in water or in phosphate buffer.

Example 4

Tensile Mechanical Properties of the Films Produced According to Example 3

The measurements of mechanical properties of crosslinked collagen films are carried out using a universal DY34-type testing machine, brand Adamel Lhomargy. The films are hydrated at room temperature in a saline phosphate buffer (PBS, pH=7.4) for 2 h. Then they are cut into 4 mm by 30 mm bands using a very sharp hole-punch. The thickness is measured on the hydrated samples. The samples are attached to a cardboard frame which aids the insertion into the jaws. The sample of film is kept hydrated. The frame is cut just before the tensile test, which takes place at a constant rate of 2 mm/min.

The initial modulus and the breaking stress are calculated from the tensile curves using the sections of the hydrated test-pieces.

The tensile properties of the films produced according to the process described in example 3 depend on the raw material (collagen or gelatin) and on the level of grafting of the collagenic precursor peptides.

The following table describes the properties of a film obtained from Example 2.

| DRY THICKNESS ($\mu$M) | WET THICKNESS ($\mu$M) | Fmax (N) | Extension (%) | σ max (MPA) | INITIAL MODULUS (MPA) |
|---|---|---|---|---|---|
| 45 | 80 | 5.4 | 42.5 | 16.7 | 25.8 |

Legend:
Fmax = maximum breaking force
σ max = maximum breaking stress

Example 5

Preparation of a Modified Collagen/Synthetic Mesh Crosslinked Composite Film for Preventing Post-operative Adhesions The process for preparing the film is identical, regardless of the nature of the raw material (collagen) and the degree of grafting of the collagenic precursor peptide. Steps 1 and 2 are identical to those described in Example 3.

Step 3 is modified in the following way:

A synthetic mesh (for example a commercially available mesh made of biodegradable polyester, 10×10 $cm^2$ in size and about 200 $\mu$m thick) is placed in each of the molds (12×12 $cm^2$).

40.0 g of filtered solution are poured onto the mesh. The molds are re-closed.

Steps 4 and 5 are identical to those described Example 3.

The oxidation can be carried out with an iodinated solution or hydrogen peroxide. Steps 6 to 11 are, depending on the method chosen, identical to those of Example 3 or of Example 4.

The films obtained are stable at room temperature. They remain stable and can be manipulated after 24 h in water or in a phosphate buffer. They have chemical properties which are superior to those of the nonreinforced membranes. They also show good resistance to tearing which means they can be sutured with great ease. They can be rolled up on themselves, which makes it possible to introduce them in trocars.

Example 6

Preparation of a Liquid Form Using Modified Collagen which is Crosslinkable In Situ, for Preventing Post-operative Adhesions The process for preparing the liquid form is identical, regardless of the nature of the raw material (collagen) and the degree of grafting of the collagenic precursor peptide.

For this example, the collagenic precursor peptide (Example 1) is in the form of a sterile lyophilizate.

Step 1:

A solution of modified collagen at 85 g/l is prepared by dissolving, under sterile conditions, the lyophilizate (Example 1) in sterile water. In this example, 1.50 g of lyophilizate with an 11% water content are dissolved in 8.3 g of sterile water (degassed beforehand with a sterile nitrogen stream). The solution is stirred in a closed container at 45° C. for 15 min, in order to obtain complete dissolution. The pH of the solution is adjusted to 7 with 5.9 ml of 0.1N sodium hydroxide sterilized by filtration over 0.2 microns.

Steps 2 and 3:

The filtration and concentration steps do not take place in this example, given that the starting lyophilizate is sterile and dissolved at the intended final concentration under sterile conditions.

Step 4:

The solution is distributed into hermetically sealed, sterile 1 ml syringes.

Example 7

The above is repeated with the difference that, in step 4, the solution is packaged, sterilely, not in syringes but in a spray bottle.

Part II: Biological Evaluation

Example 8

Experiment Concerning a Collagen Film According to the Invention as Obtained in Example 3

The aim of this study is to evaluate the post-surgical adhesion prevention properties of a collagen film according to the invention, as obtained in Example 3.

This study is carried out in the female rat, at a peritoneal site, for a period of observation of at least 2 weeks.

The effectiveness of the product is estimated by macroscopic observation of the possible adhesions at the sites of application.

The following will be studied: frequency, extent and severity of the adhesions developed.

Traumatic lesions of the peritoneal serosa are made at the level of the uterine horns and of a parietal window in female rats.

The film is positioned in such a way as to separate the parietal and uterine lesions engendered, for a period of at least 2 weeks.

A control site and a test site are prepared on each female rat. Once the at least two week period has passed, the animals are sacrificed by injecting a lethal dose of barbiturates.

The severity of the adhesions is evaluated by grading from 0 to 3:

0: absence of adhesion,
1: discrete adhesions, cleavable by blunt dissection,
2: moderate adhesions, requiring a partial sharp dissection,
3: severe adhesions, not cleavable without extended sharp dissection.

In order to express the results, the grades for the 10 control sites are added together and then the mean is determined. This mean value therefore corresponds to the mean severity of the adhesions.

For the controls, the mean grade obtained is 2.2. In addition, all the sites studied exhibit adhesions over 95% of the surface of the lesion.

For the test sites, the mean grade is 0.22.

It will be noted that only 3 out of 10 sites studied exhibited adhesions and that these adhesions were present only over about 10% of the surface area of the lesion.

In conclusion, a 90% decrease in the strength of the adhesions and also a very significant decrease in the number and in the surface area of these adhesions is obtained.

Example 9

Experiment Concerning a Modified Collagen/Mesh Film According to the Invention, as Obtained in Example 5

The aim of this study is to evaluate the post-surgical adhesion prevention properties of a modified collagen/mesh film according to the invention described in Example 5.

This study is carried out in the female rat, at a peritoneal site, for a period of observation of at least 2 weeks.

The effectiveness of the product is estimated by macroscopic observation of the possible adhesions at the sites of application.

The following will be studied: frequency, extent and severity of the adhesions developed.

Traumatic lesions of the peritoneal serosa are made at the level of the uterine horns and of a parietal window in female rats. The modified collagen/mesh film is then positioned in such a way as to separate the parietal and uterine lesions engendered, for a period of at least 2 weeks. A control site and a test site are prepared on each female rat.

Once the at least two week period has passed, the animals are sacrificed by injecting a lethal dose of barbiturates.

The severity of the adhesions is evaluated by grading from 0 to 3:

0: absence of adhesion,
1: discrete adhesions, cleavable by blunt dissection,
2: moderate adhesions, requiring a partial sharp dissection,
3: severe adhesions, not cleavable without extended sharp dissection.

In order to express the results, the grades for the 10 control sites are added together and then the mean is determined. This mean value therefore corresponds to the mean severity of the adhesions.

For the controls, the mean grade obtained is 2.2. In addition, all the sites studied exhibit adhesions over 0% of the surface of the lesion.

For the test sites, the mean grade is 0.1.

It will be noted that only 3 out of 20 sites studied exhibited adhesions and that these adhesions were present only over about 10% of the surface area of the lesion.

In conclusion, a 96% decrease in the strength of the adhesions and also a very significant decrease in the surface area of the adhesions present are obtained.

Example 10

Experiment Concerning the Liquid Form According to the Invention, as Obtained in Example 6

The aim of this study is to evaluate the post-surgical adhesion prevention properties of the liquid form according to the invention described in Example 6.

This study is carried out in the female rat, at a peritoneal site, for a period of observation of at least 2 weeks.

The effectiveness of the product is estimated by macroscopic observation of the possible adhesions at the sites of application.

The following will be studied: frequency, extent and severity of the adhesions developed.

Traumatic lesions of the peritoneal serosa are made at the level of the uterine horns and of a parietal window in female rats. Before using the solution, the syringes are reheated at 37° C. in a water bath, in order to recover a viscous solution. This solution can be applied onto a support. The viscosity of this solution allows it to form a deposit, while at the same time guaranteeing a sufficient thickness. 300 $\mu$l of this solution is then positioned in such a way as to separate the parietal and uterine lesions engendered, for a period of at least two weeks. The crosslinking of the deposit is carried out by spraying a 1% hydrogen peroxide solution. The gelling of the deposit is almost instantaneous. A homogeneous collagen hydrogel is obtained. A control site and a test site are prepared on each female rat.

Once the at least two week period has passed, the animals are sacrificed by injecting a lethal dose of barbiturates.

The severity of the adhesions is evaluated by grading from 0 to 3:

0: absence of adhesion,
1: discrete adhesions, cleavable by blunt dissection,
2: moderate adhesions, requiring a partial sharp dissection,
3: severe adhesions, not cleavable without extended sharp dissection.

In order to express the results, the grades for the 10 control sites are added together and then the mean is determined. This mean value therefore corresponds to the mean severity of the adhesions.

For the controls, the mean grade obtained is 2.2. In addition, all the sites studied exhibit adhesions over 90% of the surface of the lesion.

For the test sites (300 $\mu$l of collagen hydrogel), the mean grade is 0.7.

It will be noted that only 7 out of 10 sites studied exhibited adhesions and that these adhesions were present only over about 30% of the surface of the lesion. In conclusion, a 70% decrease in the strength of the adhesions and also a very significant decrease in the surface area of the adhesions present are obtained.

What is claimed is:

1. A means for preventing post-surgical adhesions, comprising at least one collagenic peptide which is modified by grafting free or substituted thiol functions, which is crosslinkable and/or at least partly crosslinked and the thiol functions of which are provided by mercaptoamino residues exclusively grafted onto the aspartic and glutamic acids of the collagenic chains, via amide bonds.

2. The means according to claim 1, wherein at least some of the modified collagenic peptide is in the form of a precursor A onto which are grafted mercaptoamino residues bearing substituted thiol functions, at least some of these mercaptoamino residues corresponding to formula (I):

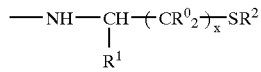

in which:
x=1 or 2,
$R^0$=H or $CH_3$,
$R^1$ represents H or $COOR^3$ with $R^3$ corresponding to a hydrocarbon-based radical of the aliphatic, aromatic or alicyclic type,
$R^2$ is an aliphatic, alicyclic, and/or aromatic radical.

3. The means according to claim 1, wherein at least some of the modified collagenic peptide is in the form of a precursor A onto which are grafted mercaptoamino residues bearing substituted thiol functions, at least some of these mercaptoamino residues corresponding to formula (I)

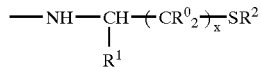

in which:
x=1 or 2,
$R^0$=H or $CH_3$
$R^1$ represents H or $COOR^3$ with $R^3$ corresponding to a hydrocarbon-based radical of the aliphatic, aromatic or alicyclic type,
$R^2$ corresponds to the following formula (II)

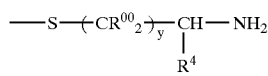

with y, $R^{00}$ and $R^4$ corresponding to the same definition as that given in the legend in formula (I) for x, $R^0$ and $R^1$.

4. The means according to claim 1, wherein at least some of the modified collagenic peptide is in the form of a precursor A onto which are grafted mercaptoamino residues chosen from the group of the following radicals:

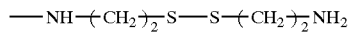

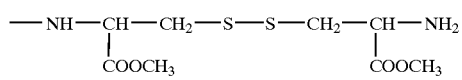

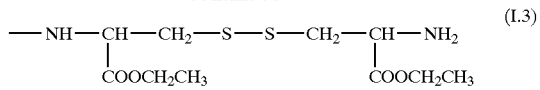

5. The means according to claim 1, wherein at least some of the collagenic peptide is in a thiol-type intermediate crosslinkable precursor form B, onto which are grafted mercaptoamino residues, at least some of which correspond to the general formula (I)

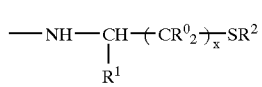

in which:
x=1 or 2,
$R^0$=H or $CH_3$,
$R^1$ represents H or $COOR^3$ with $R^3$ corresponding to a hydrocarbon-based radical of the aliphatic, aromatic or alicyclic type, a hydrogen, or a cation capable of forming a salt with $COO^-$, and
$R^2$=H.

6. The means according to claim 1, wherein at least some of the modified collagenic peptide is in a crosslinked form C comprising collagenic chains attached to one another by disulfide bridges, the constituent sulfur atoms of which belong to mercaptoamino residues exclusively grafted onto the aspartic and glutamic acids of the collagenic chains, via amide bonds.

7. The means according to claim 1, wherein at least some of the modified collagenic peptide is in a crosslinked form C comprising collagenic chains attached to one another by disulfide bridges, the constituent sulfur atoms of which belong to mercaptoamino residues exclusively grafted onto the aspartic and glutamic acids of the collagenic chains, via amide bonds, this collagenic peptide in C form being obtained from a thiol-type intermediate crosslinkable precursor form B, onto which are grafted mercaptoamino residues, at least some of which correspond to the general formula (I)

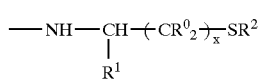

in which:
x×1 or 2,
$R^0$=H or $CH_3$,
$R^1$ represents H or $COOR^3$ with $R^3$ corresponding to a hydrocarbon-based radical of the aliphatic, aromatic or alicyclic type, a hydrogen, or a cation capable of forming a salt with $COO^-$, and
$R^2$=H.

8. The means according to claim 1, wherein at least some of the collagenic peptide also carries grafts G attached to at least some of the free amine units of the collagenic chain, via amide bonds, G being an acyl comprising a hydrocarbon-based entity, that does not contain mercaptoamino residues.

9. The means according to claim 1, wherein at least some of the collagenic peptide also carries grafts G attached to at least some of the free amine units of the collagenic chain, via amide bonds, G being an acyl comprising a hydrocarbon-based entity, that contains hetero atoms, but does not contain mercaptoamino residues.

10. The means according to claim 1, wherein at least some of the collagenic peptide also carries grafts G attached to at least some of the free amine units of the collagenic chain, via amide bonds, G corresponding to the following formula (III)

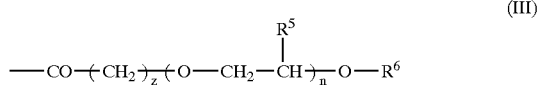
(III)

with:
$R^5$=H or $CH_3$;
$R^6$=H, or a linear or branched alkyl radical;
z=0, 1 or 2, and n>0.

11. The means according to claim 1, wherein the means is in the form of a film.

12. The means according to claim 1, further comprising a composite comprising a matrix comprising the collagenic peptide as defined in claim 1, and a reinforcement material included in the matrix, wherein the reinforcement material is a biodegradable polymer.

13. The means according to claim 1, further comprising a composite comprising a matrix comprising the collagenic peptide as defined in claim 1, and a reinforcement material included in the matrix, wherein the reinforcement material is a biodegradable material in the form of a fibrous substance, which is woven or nonwoven.

14. The means according to claim 1, further comprising a composite comprising a matrix comprising the collagenic peptide as defined in claim 1, and a reinforcement material included in the matrix, wherein the reinforcement material is a biodegradable material in the form of a fibrous substance, which is woven with knitted stitches.

15. The means according to claim 1, further comprising a composite comprising a matrix comprising the collagenic peptide as defined in claim 1, and a reinforcement material included in the matrix, wherein the reinforcement material is an α-hydroxycarboxylic polymer.

16. The means according to claim 1, further comprising a composite comprising a matrix comprising the collagenic peptide as defined in claim 1, and a reinforcement material included in the matrix, wherein the reinforcement material is polylactic acid and/or polyglycolic acid.

17. The means according to claim 1, further comprising a composite comprising a matrix having a surface, the matrix comprising the collagenic peptide as defined in claim 1, and a fibrous reinforcement material included in the matrix, wherein the reinforcement material is a biodegradable material in the form of a film, and the fibrous reinforcement is present on a part of the surface of the matrix.

18. The means according to claim 1, wherein the means is in a nonsolid form which is crosslinkable, and/or at least partly crosslinked, and which can be applied and/or implantable onto and/or into a support.

19. The means according to claim 1, wherein the means is in a nonsolid form which is crosslinkable, and/or at least partly crosslinked, and which can be applied and/or implantable onto and/or into a support, and comprises collagenic peptide in liquid form.

20. The means according to claim 1, wherein the means is in a nonsolid form which is crosslinkable, and/or at least partly crosslinked, and which can be applied and/or implantable onto and/or into a support, and comprises collagenic peptide in the form of a gel.

21. The means according to claim 18, further comprising at least one tool for storing and for applying into and/or onto a support, a nonsolid form of the crosslinkable and/or at least partly crosslinked collagenic peptide.

22. The means according to claim 21, further comprising an oxidizing agent for crosslinking the collagenic peptide.

23. A process for preparing the means for preventing post-surgical adhesions according to claim 1, comprising:
a) preparing a solution of crosslinkable precursor of modified collagenic peptide;
b) molding the solution into an intended configuration;
c) crosslinking the solution; and
d) optionally, washing to remove an oxidizing agent when used to crosslink the solution.

24. A process for preparing the means for preventing post-surgical adhesions according to claim 1, comprising:
a) preparing a solution of crosslinkable precursor of modified collagenic peptide;
b) filtering the solution so as to extract therefrom the elements which are greater than or equal to 0.8 µm in size;
c) molding the filtrate into an intended configuration;
d) gelling the molded solution, by decreasing its temperature below its gelling temperature;
e) eliminating solvent;
f) crosslinking the solution;
g) optionally, washing to remove an oxidizing agent when used to crosslink the solution;
h) impregnating the solution which is crosslinked, or which is in the process of being crosslinked, using a solution of at least one plasticizer;
i) drying the crosslinked material;
j) cutting the crosslinked material to a size for use; and
k) sterilizing the crosslinked material by radiation.

25. A process for preparing a means according to claim 1, wherein the means is in a nonsolid form which is crosslinkable, and/or at least partly crosslinked, and which can be applied and/or implantable onto and/or into a support, comprising:
a) preparing a solution of crosslinkable precursor of modified collagenic peptide; and
b) packaging the solution sterilely under an inert atmosphere.

26. A process for preparing a means according to claim 1, wherein the means is in a nonsolid form which is crosslinkable, and/or at least partly crosslinked, and which can be applied and/or implantable onto and/or into a support, comprising:
a) preparing a solution of crosslinkable precursor of modified collagenic peptide;
b) filtering the solution so as to extract therefrom the elements which are greater than or equal to 0.8 µm in size;
c) concentrating the solution; and
d) packaging the solution sterilely under an inert atmosphere.

27. The process according to claim 26, wherein the packaged solution is applied onto a support and crosslinking is brought about using a biocompatible oxidizing agent.

* * * * *

UNITED STATES PATENT AND TRADEMARK OFFICE
CERTIFICATE OF CORRECTION

PATENT NO.    : 6,790,438 B1
DATED         : September 14, 2004
INVENTOR(S)   : Constancis et al.

It is certified that error appears in the above-identified patent and that said Letters Patent is hereby corrected as shown below:

Column 22,
Line 51, "x×1 or 2," should read -- x = 1 or 2, --.
Line 63, "entity, that" should read -- entity that --.

Column 23,
Line 1, "entity, that" should read -- entity that --.

Column 24,
Line 25, "solution, by" should read -- solution by --.

Signed and Sealed this

Seventh Day of December, 2004

JON W. DUDAS
*Director of the United States Patent and Trademark Office*